United States Patent [19]

Rieber et al.

[11] 4,380,642
[45] Apr. 19, 1983

[54] SIMULTANEOUS PREPARATION OF PYRAZOLE AND TRIAZOLES

[75] Inventors: Norbert Rieber; Rolf Platz, both of Mannheim; Werner Fuchs, Ludwigshafen, all of Fed. Rep. of Germany

[73] Assignee: BASF Aktiengesellschaft, Ludwigshafen, Fed. Rep. of Germany

[21] Appl. No.: 284,398

[22] Filed: Jul. 17, 1981

[30] Foreign Application Priority Data

Aug. 20, 1980 [DE] Fed. Rep. of Germany ....... 3031347

[51] Int. Cl.³ ................. C07D 249/04; C07D 249/06; C07D 231/12
[52] U.S. Cl. .................................. 548/255; 544/233; 548/373
[58] Field of Search ....................... 548/255, 257, 373; 544/233, 234

[56] References Cited

U.S. PATENT DOCUMENTS 4,189,434 2/1980 Platz et al. ..................... 548/257

FOREIGN PATENT DOCUMENTS 557338 8/1932 Fed. Rep. of Germany .
557814 8/1932 Fed. Rep. of Germany .

OTHER PUBLICATIONS

Chemical Communications, (1969), p. 72.
Ullmanns Encyklopädie der technischen Chemie, vol. 8, pp. 498–500.

*Primary Examiner*—Donald G. Daus
*Assistant Examiner*—M. C. Eakin
*Attorney, Agent, or Firm*—John H. Shurtleff

[57] ABSTRACT

A process for the simultaneous preparation of pyrazole and triazoles by reacting a triazoline compound with a basic compound and then oxidizing the product with hydrogen peroxide.

The triazoles and pyrazole obtainable by the process of the invention are valuable starting materials for the preparation of dyes, pesticides and drugs.

8 Claims, No Drawings

SIMULTANEOUS PREPARATION OF PYRAZOLE AND TRIAZOLES

The invention relates to a novel process for the simultaneous preparation of pyrazole and triazoles by reacting a triazoline compound with a basic compound and then oxidizing the product with hydrogen peroxide.

Chem. Communications, (1969), 72 discloses that the bis-azo compound of the formula

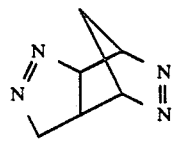

can be decomposed, by heating for 5 hours under nitrogen at 120° C., to pyrazole and a tricyclic diazoline derivative, in the ratio of 25:75:

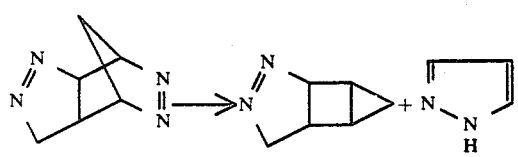

We have found that pyrazole and triazoles of the formula

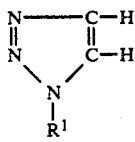   I where $R^1$ is hydrogen or an aliphatic, cycloaliphatic, araliphatic or aromatic radical, are obtained simultaneously, in an advantageous manner, if, in a first step, a triazoline compound of the formula

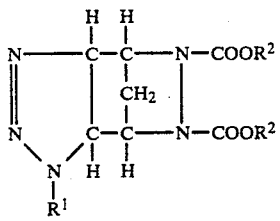   II where $R^1$ has the above meanings and $R^2$ is hydrogen or an aliphatic radical, is reacted with a basic compound and thereafter, in a 2nd step, the product is oxidized with hydrogen peroxide.

Where 6-phenyl-2,3-dicarbomethoxy-2,3,6,7,8-pentaza-tricyclo-[5.2.1.0^{5,9}]-deca-7-ene and sodium hydroxide are used, the reaction can be represented by the following equations:

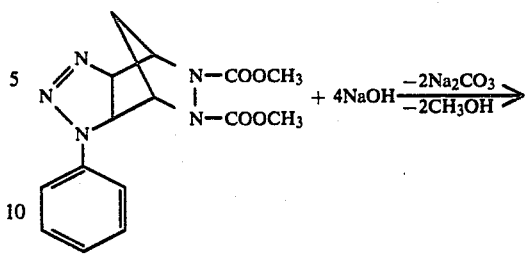

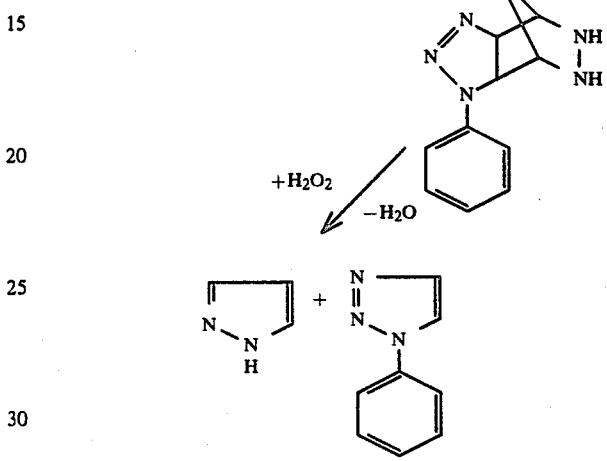

Compared to the conventional process, the process according to the invention gives pyrazole and triazoles simultaneously, in a simple and economical manner, in better yield and greater purity. All these advantageous results are surprising in view of the prior art.

The starting materials II are easily obtainable by adduct formation of an organic azide with an N,N'-dialkoxycarbonyl-2,3-diaza-bicyclo-[2,2,1]-heptene (German Pat. No. 557,338), or, where $R^1$ in the starting material is hydrogen, by adduct formation of trimethylsilyl azide with the above bicycloheptene, followed by ethanolysis of the silicon substituents.

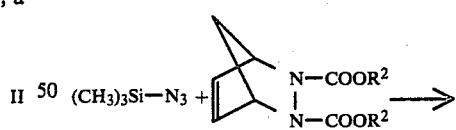

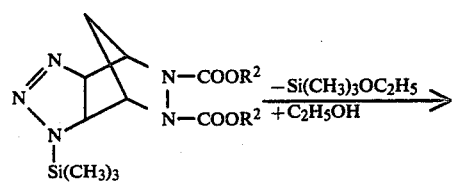

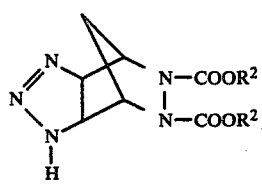

Preferred starting materials II and accordingly preferred end products I are those where the individual radicals $R^1$ and $R^2$ can be identical or different and each is hydrogen or alkyl of 1 to 18, advantageously 1 to 12, especially 1 to 4, carbon atoms, and $R^1$ can also be cycloalkyl of 5 to 8 carbon atoms, aralkyl or alkylaryl of 7 to 12 carbon atoms, or phenyl or naphthyl which are unsubstituted or substituted by from 1 to 5 bromine atoms, fluorine atoms, chlorine atoms, iodine atoms, nitro groups, dialkylamino groups and/or alkoxy groups of 1 to 4 carbon atoms. The above radicals can additionally be substituted by groups which are inert under the reaction conditions, for example halogen, nitro or alkyl or alkoxy each of 1 to 4 carbon atoms.

Examples of suitable starting materials II are 2,3-dicarbomethoxy-2,3,6,7,8-pentaza-tricyclo-8 5.2.1.0$^{5.9}$]-deca-7-ene which is unsubstituted or is 6-substituted by methyl, ethyl, propyl, isopropyl, butyl, sec.-butyl, tert.-butyl, isobutyl, pentyl, hexyl, heptyl, octyl, nonyl, decyl, undecyl, dodecyl, cyclohexyl, cyclopentyl, cyclopropyl, benzyl, phenyl, 2'-, 3'- or 4'-chlorophenyl, o-, m- or p-methylphenyl, o-, m- or p-nitrophenyl or naphthyl, and the homologous diethyl, dipropyl, diisopropyl, dibutyl, diisobutyl, di-sec.-butyl and di-tert.-butyl esters of the above decenes.

The reaction is advantageously carried out at from $-20°$ to $+140°$ C., preferably from $40°$ to $100°$ C., in both stages, under atmospheric or superatmospheric pressure, continuously or batchwise. Advantageously, a solvent which is inert under the reaction conditions is employed. Examples of suitable solvents are water, alkanols and cycloalkanols, eg. ethanol, methanol, n-butanol, isobutanol, tert.-butanol, glycol, glycerol, n-propanol, isopropanol, amyl alcohol and cyclohexanol, and corresponding mixtures. The solvent is advantageously used in an amount of from 100 to 10,000 percent by weight, preferably from 200 to 2,000 percent by weight, based on starting material II. Advantageously, the solvent or a part of the solvent is employed in the form of the solution of the peroxide or of the basic compound.

The first stage of the reaction is carried out with a basic compound, advantageously using from 4 to 20, preferably from 4 to 8, equivalents of the latter per mole of starting material II. Preferred basic compounds are alkaline earth metal compounds, ammonium compounds and especially alkali metal compounds, as well as corresponding mixtures. Specific examples are potassium hydroxide, sodium hydroxide, potassium carbonate, sodium carbonate, lithium hydroxide, lithium carbonate, calcium hydroxide, calcium oxide, barium oxide and barium hydroxide.

The 2nd stage of the reaction is carried out with hydrogen peroxide. The latter is advantageously used in the form of an aqueous solution of from 5 to 60, preferably from 10 to 55, percent strength by weight. Compounds which form hydrogen peroxide under the reaction conditions can also be used where appropriate, for example inorganic or organic peroxo compounds such as sodium peroxide, potassium peroxide, magnesium peroxide, calcium peroxide, zinc peroxide, barium peroxide; hydroperoxide, eg. NaOOH.0.5 $H_2O_2$ or NH$_4$OOH; corresponding hydrates, such as CaO$_2$.8-H$_2$O and peroxo-hydrates, such as BaO$_2$.H$_2$O$_2$ and BaO$_2$.2H$_2$O$_2$; peroxocarbonates, such as sodium peroxocarbonate and calcium peroxocarbonate; and peroxophosphates, such as potassium peroxodiphosphate. It is also possible to use hydrogen peroxide adducts, such as sodium borate peroxohydrate and sodium carbonate peroxohydrate.

The reaction can be carried out as follows: a mixture of the starting material II, basic compound and solvent is kept at the reaction temperature of the first stage for from 1 to 6 hours. Hydrogen peroxide, advantageously together with solvent or as an aqueous solution, is then added and the 2nd stage of the reaction is carried out at its appropriate temperature for from 0.5 to 2 hours. Pyrazole and end product I are isolated from the reaction mixture in a conventional manner, for example by filtering, acidifying and concentrating the filtrate, neutralizing the residue and extracting it.

Pyrazole, and the triazoles I, obtained by the process of the invention, are valuable starting materials for the preparation of dyes, pesticides and drugs. Concerning their use, reference may be made to the above publications and to Ullmanns Encyklopädie der technischen Chemie, volume 8, pages 498–500.

In the Examples which follow, parts are by weight.

EXAMPLE 1

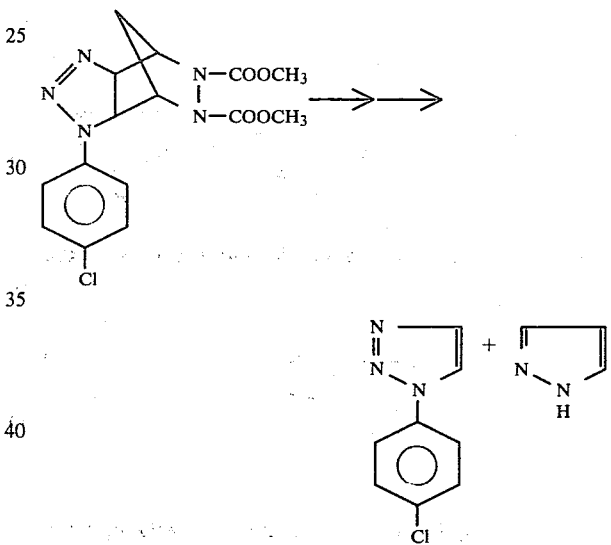

25 parts of 6-(4-chlorophenyl)-2,3-dicarbomethoxy-2,3,6,7,8-pentaza-tricyclo-[5.2.1.0$^{5.9}$]-deca-7-ene, 22 parts of 50 percent strength by weight aqueous sodium hydroxide solution and 120 parts of methanol are heated for 5 hours at 68° C., with stirring. 7 parts of $H_2O_2$ in 40 parts of water are then added at 68° C., the mixture is stirred for one hour at 68° C., 500 parts of water are added and the mixture is cooled to 0° C. The filter precipitate is filtered off, washed alkali-free with water and dried. 12 parts (97% of theory) of p-chlorophenyl-triazole, of melting point 111° C., are obtained. The filtrate is acidified with 3.5 percent strength by weight aqueous hydrochloric acid and concentrated in a rotary evaporator at 40° C. and under 15 mbar. The residue is dissolved in 100 parts of water and neutralized with aqueous sodium hydroxide solution, and the mixture is extracted four times with 100 parts of CH$_2$Cl$_2$. Concentrating the CH$_2$Cl$_2$ extract gives 4.2 parts (90% of theory) of pyrazole, of melting point 69° C.

EXAMPLES 2 TO 12

The reactions shown in the Table are carried out similarly to Example 1.

TABLE

| Example | R[1] | Parts of starting material II | Triazole I Yield in % of theory | Triazole I Melting point (°C.) or 1H—NMR (δ in ppm) | Pyrazole Yield in % of theory | Pyrazole Melting point (°C.) |
|---|---|---|---|---|---|---|
| 2 | n-C$_{12}$H$_{25}$— | 50 | 93 | 44 | 90 | 69 |
| 3 | C$_6$H$_5$— | 50 | 87 | 47 | 85 | 69 |
| 4 | o-CH$_3$—C$_6$H$_4$(a) | 60 | 76 | oil, 2.2(s,3H) 7.3(s,4H), 7.7(s,2H) | 78 | 69 |
| 5 | m-CH$_3$—C$_6$H$_4$(a) | 50 | 71 | oil, 2.35(s,3H), 7.3(m,4H), 7.7(s,1H), 7.9(s,1H) | 70 | 69 |
| 6 | 1-Naphthyl | 20 | 90 | 56 | 88 | 69 |
| 7 | Cyclohexyl | 20 | 95 | 34 | 91 | 69 |
| 8 | Benzyl | 15 | 79 | 60 | 70 | 69 |
| 9 | Methyl(b) | 50 | 82 | 228 | 79 | 69 |
| 10 | n-Propyl(b) | 40 | 87 | b.p. 113° C./14 mm Hg | 83 | 69 |
| 11 | 2,4-Dichlorophenyl | 20 | 89 | 80 | 84 | 69 |
| 12 | 4-Nitrophenyl | 20 | 78 | 203 | 75 | 69 |

(a)These compounds separate out as oils on cooling.
(b)These compounds are isolated by extraction with CH$_2$Cl$_2$.

We claim:

1. A process for the simultaneous preparation of pyrazole and triazoles of the formula

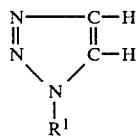   I where
R[1] is:
hydrogen; or
alkyl of 1 to 18 carbon atoms, cycloalkyl of 5 to 8 carbon atoms, aralkyl or alkylaryl of 7 to 12 carbon atoms; or
phenyl or naphthyl which are unsubstituted or substituted by from 1 to 5 bromine atoms, fluorine atoms, chlorine atoms, iodine atoms, nitro groups, dialkylamino groups of 1 to 4 carbon atoms per alkyl group and/or alkoxy groups of 1 to 4 carbon atoms, and where R[1] may be additionally substituted by halogen, nitro or alkyl or alkoxy each of 1 to 4 carbon atoms, which process comprises a first step of reacting a triazoline compound of the formula

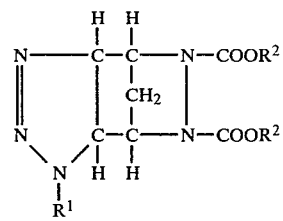   II where R[1] has the above meaning and R[2] is hydrogen, alkyl of 1 to 18 carbon atoms or said alkyl additionally substituted by halogen, nitro or alkyl or alkoxy each of 1 to 4 carbon atoms, with a basic compound and, thereafter, a second step of oxidizing the product of said first step with hydrogen peroxide.

2. A process as claimed in claim 1 wherein said basic compound is selected from the group consisting of alkaline earth metal compounds, ammonium compounds, alkali metal compounds and mixtures thereof.

3. A process as claimed in claim 1 or 2 wherein the reaction is carried out at from −20° to +140° C. in an inert solvent, using from 4 to 20 equivalents of said basic compound per mole of starting material II in the first step and using hydrogen peroxide as a 5–60 percent strength by weight aqueous solution in the second step.

4. A process as claimed in claim 1, wherein the reaction is carried out at from −20° to +140° C.

5. A process as claimed in claim 1, wherein the reaction is carried out at from 40° to 100° C.

6. A process as claimed in claim 1, wherein the reaction is carried out using a solvent which is inert under the reaction conditions.

7. A process as claimed in claim 1, wherein the reaction is carried out in the presence of from 4 to 20 equivalents of a basic compound per mole of starting material II.

8. A process as claimed in claim 1, wherein the hydrogen peroxide is used as a 5–60 percent strength by weight aqueous solution.

* * * * *